United States Patent
Bogan, Jr.

(10) Patent No.: US 9,517,451 B2
(45) Date of Patent: Dec. 13, 2016

(54) PREPARATION OF PROPANE OXIDATION CATALYSTS

(71) Applicant: Rohm and Haas Company, Philadelphia, PA (US)

(72) Inventor: Leonard E. Bogan, Jr., Midland, MI (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/430,600

(22) PCT Filed: Sep. 5, 2013

(86) PCT No.: PCT/US2013/058195
§ 371 (c)(1),
(2) Date: Mar. 24, 2015

(87) PCT Pub. No.: WO2014/051955
PCT Pub. Date: Apr. 3, 2014

(65) Prior Publication Data
US 2015/0273445 A1  Oct. 1, 2015

Related U.S. Application Data

(60) Provisional application No. 61/707,053, filed on Sep. 28, 2012.

(51) Int. Cl.
| | | |
|---|---|---|
| *B01J 21/00* | (2006.01) | |
| *B01J 23/00* | (2006.01) | |
| *B01J 23/06* | (2006.01) | |
| *B01J 23/08* | (2006.01) | |
| *B01J 23/12* | (2006.01) | |
| *B01J 23/14* | (2006.01) | |
| *B01J 23/16* | (2006.01) | |
| *B01J 23/48* | (2006.01) | |
| *B01J 23/70* | (2006.01) | |
| *B01J 23/76* | (2006.01) | |
| *B01J 37/00* | (2006.01) | |
| *B01J 37/08* | (2006.01) | |
| *B01J 37/12* | (2006.01) | |
| *B01J 27/057* | (2006.01) | |
| *B01J 23/28* | (2006.01) | |
| *B01J 35/00* | (2006.01) | |
| *C07C 51/215* | (2006.01) | |

(52) U.S. Cl.
CPC ............ *B01J 27/0576* (2013.01); *B01J 23/28* (2013.01); *B01J 35/002* (2013.01); *B01J 37/0045* (2013.01); *B01J 37/08* (2013.01); *C07C 51/215* (2013.01); *B01J 37/086* (2013.01); *B01J 2523/00* (2013.01)

(58) Field of Classification Search
CPC ............ B01J 6/001; B01J 21/00; B01J 23/00; B01J 23/06; B01J 23/08; B01J 23/10; B01J 23/12; B01J 23/14; B01J 23/16; B01J 23/28; B01J 23/48; B01J 23/70; B01J 23/76; B01J 37/00; B01J 37/08; B01J 37/12
USPC .................................. 502/305-355
See application file for complete search history.

(56) References Cited

U.S. PATENT DOCUMENTS

| | | | | |
|---|---|---|---|---|
| 4,065,468 A | * | 12/1977 | Grasselli | ................... B01J 23/24 502/206 |
| 4,170,570 A | * | 10/1979 | Zagata | .................... B01J 23/28 502/211 |
| 4,918,214 A | * | 4/1990 | Brazdil, Jr. | ............ B01J 23/002 558/319 |
| 5,049,692 A | | 9/1991 | Hatano et al. | |
| 5,380,933 A | | 1/1995 | Ushikubo et al. | |
| 5,637,546 A | | 6/1997 | Tenten et al. | |
| 5,994,580 A | | 11/1999 | Takahashi et al. | |
| 6,036,880 A | | 3/2000 | Komada et al. | |
| 6,060,422 A | | 5/2000 | Takahashi et al. | |
| 6,063,728 A | | 5/2000 | Hinago et al. | |
| 6,291,393 B1 | | 9/2001 | Tu et al. | |
| 6,310,241 B1 | * | 10/2001 | Karim | .................... B01J 23/002 562/549 |
| 6,346,647 B2 | | 2/2002 | Tu et al. | |
| 6,407,280 B1 | | 6/2002 | Chaturvedi et al. | |
| 6,504,053 B1 | | 1/2003 | Chaturvedi et al. | |
| 6,610,629 B2 | | 8/2003 | Hinago et al. | |
| 6,642,173 B2 | * | 11/2003 | Bogan, Jr. | .............. B01J 23/002 502/311 |
| 6,700,015 B2 | | 3/2004 | Chaturvedi et al. | |
| 6,781,017 B2 | | 8/2004 | Machhammer et al. | |
| 6,790,988 B2 | | 9/2004 | Chaturvedi et al. | |

(Continued)

FOREIGN PATENT DOCUMENTS

| | | |
|---|---|---|
| DE | 102009054229 | 3/2014 |
| JP | 2001300311 | 10/2001 |
| WO | 2009106474 | 9/2009 |

OTHER PUBLICATIONS

Havecker, et al., "Surface chemistry of phase-pure M1 MoVTeNb oxide during operation in selective oxidation of propane to acrylic acid", Journal of Catalysis, 285, 2012, p. 48-60.

Vitry, et al., "Mo—V—Te—(Nb)—O mixed metal oxides prepared by hydrothermal synthesis for catalytic selective oxidations of propane and propene to acrylic acid", Applied Catalysis A: General, 251, 2003, p. 411-424.

*Primary Examiner* — Patricia L Hailey
(74) *Attorney, Agent, or Firm* — Edward L. Brant

(57) ABSTRACT

A process for preparing a propane oxidation catalyst, the process comprising pre-calcining the catalyst precursor in an oxygen-containing gas at a temperature of less than 330° C. until the weight of the precursor stabilizes to obtain a pre-calcined precursor; then calcining the pre-calcined precursor to obtain the catalyst.

9 Claims, No Drawings

(56) References Cited

U.S. PATENT DOCUMENTS

| | | |
|---|---|---|
| 6,825,380 B2 | 11/2004 | Chaturvedi et al. |
| 6,841,699 B2 * | 1/2005 | Bogan, Jr. .............. B01J 23/002 |
| | | 502/311 |
| 7,009,075 B2 | 3/2006 | Hazin |
| 7,332,625 B2 | 2/2008 | Dubois et al. |
| 7,495,121 B2 | 2/2009 | Hibst et al. |
| 7,635,786 B2 * | 12/2009 | Shin ...................... C07C 51/215 |
| | | 562/532 |
| 2002/0161256 A1 | 10/2002 | Bogan, Jr. et al. |
| 2004/0082190 A1 | 4/2004 | Borgmeier et al. |
| 2004/0116284 A1 * | 6/2004 | Stevenson .............. B01J 23/002 |
| | | 502/311 |
| 2004/0147393 A1 | 7/2004 | Hibst et al. |
| 2006/0293538 A1 | 12/2006 | Dubois et al. |
| 2008/0064590 A1 | 3/2008 | Bogan et al. |
| 2008/0194871 A1 | 8/2008 | Dubois et al. |
| 2009/0042723 A1 | 2/2009 | Wang et al. |
| 2011/0178333 A1 | 7/2011 | Kim et al. |

\* cited by examiner

PREPARATION OF PROPANE OXIDATION CATALYSTS

CROSS-REFERENCE TO RELATED APPLICATIONS

This application claims priority from provisional application Ser. No. 61/707,053, filed Sep. 28, 2012, which is incorporated herein by reference in its entirety.

BACKGROUND OF THE INVENTION

The invention relates to the preparation of metal oxide catalysts that are useful in the oxidation of propane.

Thousands of tons of acrylic acid and acrylonitrile are produced from propylene each year. The lower price of propane relative to propylene made the development of a process starting with propane very attractive. Accordingly, a MoVTeNb mixed-metal oxide catalyst that gives good yields of acrylonitrile and acrylic acid from propane was developed and has been the subject of a significant amount of research.

In a typical catalyst synthesis, water-soluble metal precursor compounds are dissolved in water, and the resulting mixture is dried to form a solid precursor mixture of metal compounds. The precursor is heated to an intermediate temperature in air to decompose and drive off water, ammonia, and organics, and then is heated under an inert (oxygen-free) atmosphere to a higher temperature to form the mixed-metal oxide catalyst.

The Mo—V—Te—Nb—O system is complex, with multiple phases kinetically accessible under the conditions required to prepare the best catalysts. An orthorhombic phase, called M1 in the literature, has the $Cs_{0.7}(Nb_{2.7}W_{2.3})O_{14}$ structure. This phase is generally acknowledged to be necessary to activate propane. A pseudo-hexagonal phase, called M2, has a modified hexagonal tungsten bronze (HTB) structure. In addition to these, many preparations also include an $M_5O_{14}$ phase. An intergrowth tungsten bronze (ITB) phase having the formula $TeM_5O_{16}$ is sometimes seen as well. Thus, it is difficult to prepare a material having only an M1 phase on a commercial scale.

In view of the unsettled state of the art, it would be desirable to have a improved process for preparing a MoVTeNb mixed-metal oxide catalyst.

SUMMARY OF THE INVENTION

The invention is such a process for preparing a propane oxidation catalyst, the process comprising: (a) preparing a catalyst precursor; (b) pre-calcining the catalyst precursor in an oxygen-containing gas at a temperature of less than 330° C. until the weight of the precursor stabilizes to obtain a pre-calcined precursor; then (c) calcining the pre-calcined precursor to obtain the catalyst.

We have unexpectedly found that extending the hold or "soak" time in air at a temperature of less than 330° C. mitigates both the loss of Te during calcination and the formation of the less-desired phase M2. Since Te is a relatively expensive metal, mitigating its loss is desirable for lowering catalyst manufacturing costs. Mitigating the formation of phase M2 is desirable for preparing an active catalyst, as phase M2 is not active for oxidation of propane. It is counter-intuitive that this process would lead to formation of less phase M2, since higher levels of Te typically give higher levels of phase M2.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

The process of the invention employs a catalyst precursor and an oxygen-containing gas.

The term "oxygen-containing gas," as used herein, refers to any gas comprising from 0.01% up to 100% oxygen, including, for example, air. While the oxygen-containing gas may be pure oxygen gas, it is usually more economical and practical to use an oxygen-containing gas such as air. Mixtures of oxygen-containing gases may be employed.

The catalyst precursor can be prepared by methods known to those skilled in the art. For example, the catalyst precursor can be formed according to the methods described in, e.g., U.S. Pat. No. 6,825,380.

The preparation employs at least one metal oxide precursor. A metal oxide precursor is a metal-containing substance, e.g., a metal complex and/or a metal salt, that can be oxidized or decomposed to form a metal oxide, e.g., by calcination. The catalyst precursor may be prepared in the following manner. In a first step, a slurry or solution may be formed by admixing metal compounds, preferably at least one of which contains oxygen, and at least one solvent in appropriate amounts to form the slurry or solution. A solution is preferred. The metal compounds advantageously contain the elements A, N, X, Z and O as defined herein, as well as vanadium.

Suitable solvents include water; alcohols such as, for example, methanol, ethanol, propanol, and diols; and other polar solvents. Water is preferred. The water can be any water that is suitable for use in chemical synthesis including, without limitation, distilled water and deionized water. The amount of water is preferably an amount sufficient to keep the metal compounds substantially in solution long enough to avoid or minimize compositional and/or phase segregation. Thus, the amount of water employed will vary according to the amounts and solubilities of the metal compounds employed.

Once the slurry or solution is formed, the solvent is removed, by any suitable method known in the art, to form a catalyst precursor. Such methods include, without limitation, vacuum drying, freeze drying, spray drying, rotary evaporation and air drying. Vacuum drying is generally performed of pressures ranging from 10 to 500 mHg. Freeze drying typically entails freezing the solution or slurry using, for instance, liquid nitrogen and drying the frozen slurry or solution under vacuum. Spray drying is generally performed under an inert atmosphere such as nitrogen or argon, with an inlet temperature ranging from 125° C. to 200° C., and an outlet temperature ranging from 75° C. to 150° C. Rotary evaporation is generally performed at a temperature of from 25° C. to 90° C. at a pressure of from 10 to 760 mmHg. Air drying may be effected at temperatures ranging from 25° C. to 90° C. Rotary evaporation or spray drying are generally preferred.

The catalyst precursor is pre-calcined in an oxygen-containing gas at a temperature of less than 330° C. until the weight of the precursor stabilizes to obtain a pre-calcined precursor. Pre-calcining can be performed using equipment and methods well-known in the art. However, for the process of the invention it is critical that the pre-calcined precursor be held in an oxygen-containing gas at a temperature of less than 330° C. The temperature of the pre-calcination is a maximum temperature, i.e. no point in the pre-calcination equipment is higher than the specified temperature during the precalcination step.

The pre-calcining temperature can be less than 310° C., less than 300° C., less than 290° C., or less than 280° C. In various embodiments of the invention, the time of precalcination is at least 4 hours, at least 5 hours, at least 6 hours, at least 7 hours, or at least 8 hours. In one embodiment of the invention, the precalcination time is from 4 to 8 hours.

The pre-calcined precursor is calcined according to methods well known to those skilled in the art to form the catalyst. See, e.g., U.S. Pat. No. 6,825,380.

The general formula for the MMO catalyst is $A_aV_bN_cX_dZ_eO_f$ wherein A is at least one element selected from the group consisting of Mo and W, N is at least one element selected from the group consisting of Te and Sb, X is at least one element selected from the group consisting of Nb, Ta, Ti, Al, Zr, Cr, Mn, Fe, Ru, Co, Rh, Ni, Pt, Sb, Bi, B, In, As, Ge, Sn, Hf, Pb, P, Pm, Eu, Gd, Dy, Ho, Er, Tm, Yb and Lu, and Z is at least one element selected from the group consisting of Zn, Ga, Ir, Sm, Pd, Au, Ag, Cu, Sc, Y, Pr, Nd and Tb; and wherein, when a=1, b=0.01 to 1.0, c=0.01 to 1.0, d=0.01 to 1.0, e=0 to 0.1 and f is dependent on the oxidation state of the other elements. In one embodiment, the MMO is promoted, i.e. Z is present, preferably with a value of e from 0.001 to 0.1. Promoted MMO catalysts are described, e.g., in U.S. Pat. Nos. 6,825,380; 6,790,988; 6,700,015; 6,504,053 and 6,407,280. In another embodiment, Z is absent (e=0).

Preferably, when a=1, b=0.1 to 0.5, c=0.05 to 0.5, d=0.01 to 0.5 and e=0.001 to 0.02. More preferably, when a=1, b=0.15 to 0.45, c=0.05 to 0.45, d=0.05 to 0.2 and e=0.005 to 0.015. However, in an alternative embodiment, when a=1 and e=0, b=0.01 to 1.0, c=0.01 to 1.0 and d=0.01 to 1.0; preferably, when a=1 and e=0, b=0.1 to 0.5, c=0.05 to 0.5 and d=0.01 to 0.5; more preferably, when a=1 and e=0, b=0.15 to 0.45, c=0.05 to 0.45 and d=0.05 to 0.2. Moreover, in a further alternative embodiment, e=0.005 to 0.1; more preferably, e=0.01 to 0.05. The value of f, i.e. the amount of oxygen present, is dependent on the oxidation state of the other elements in the catalyst. However, f is typically in the range of from 3 to 4.7. Preferably, A is Mo. Preferably, N is Te. Preferably, X is Nb or Ta; and most preferably, X is Nb. In one preferred embodiment of the invention, the catalyst is $Mo_aV_bTe_cNb_dZ_eO_f$. Preferably, Z is Pd. In another embodiment of the invention, the catalyst is $Mo_aV_bTe_cNb_dO_f$ (e=0).

SPECIFIC EMBODIMENTS OF THE INVENTION

The following examples are given to illustrate the invention and should not be construed as limiting its scope.

Phase Composition Determination Method

The relative weight percentages of phases M2 and M1 can be determined from the ratio of powder x-ray diffraction (XRD) peak intensities at 28.3° and 27.1° two theta according to the correlation:

Wt. % $M2$=100×wt. phase $M2$/(wt. phases $M1$ and $M2$)=−5.9783+[20.627×$(I_{28.3}/I_{27.1})$]−[1.2311×$(I_{28.3}/I_{27.0})^2$]

This formula was developed based on blending pure phases and correlating the weight ratios of the known blends to the $(I_{28.3}/I_{27.1})$ intensity ratio. The following values are used to demonstrate the calculation, based on values for the catalyst of Example 3.

$I_{28.3}$=2774
$I_{27.1}$=4120
$I_{28.3}/I_{27.1}$=0.6733

100×wt. phase $M2$/(wt. phases $M1$ and $M2$)=−5.9783+(20.627×0.6733)−(1.2311×0.6733×0.6733)=7.35

The total amount of $M_5O_{14}$ phase is determined from the ratio of powder x-ray diffraction (XRD) peak intensities at 24.8° and 25.2° two theta according to the correlation Wt. % $M_5O_{14}$=100×wt. $M_5O_{14}$ phase/total=−7.0767+[20.55×$(I_{24.8}/I_{25.2})$]

$I_{24.8}$=510
$I_{25.2}$=1191
$I_{24.8}/I_{25.2}$=0.4282%

% $M_5O_{14}$ phase=−7.0767+(20.55×0.4282)=1.72

The amount of phase M2 is determined by subtracting the amount of $M_5O_{14}$ phase from the total, and multiplying the remainder by the % phase M2/(phases M1 and M2).

% $M_5O_{14}$ phase=1.7%
% phase M1 plus phase M2)=98.3%
% phase M2=0.0735×98.3%=7.2%
% phase M/=98.3−7.2=91.1
All results ±2% (i.e. % phase M1=91.1±2%)

Preparation of Catalyst Precursor

Ammonium heptamolybdate tetrahydrate (1400 g), telluric acid (384.2 g) ammonium metavanadate (264.3 g), and conc. nitric acid (323.2 g) are dissolved sequentially in water (7850 g) at 70° C. to make solution A. In a separate tank, ammonium niobium oxalate (613.7 g) and oxalic acid dihydrate (155.4 g) are dissolved in water (7065 g) at ambient temperature to make solution B. In a third tank, solution A (4500 g) and solution B (3450 g) are mixed, and this mixture is fed to a spray-drier to yield a green-orange powder (977 g).

The powder is subjected to an initial heat treatment in air to remove materials other than metal oxides (primarily water, ammonia, and oxalic acid) prior to calcination. The green-orange powder (300 g) is heated in a ceramic dish in a box furnace under static air for one hour at 275° C. (ramp rate 10° C./min) to yield about 205 g of olive green powder. This procedure is repeated many times to treat all of the powder. The bulk elemental composition of the precursor, measured by x-ray fluorescence (XRF), is $Mo_{0.70}V_{0.19}Te_{0.17}Nb_{0.12}$.

Example 1

In a Lindberg/Blue M Mini-Mite tube furnace, precursor (12.0 g) is calcined in a one-inch diameter quartz tube. The furnace is mounted so that the long axis of the tube is oriented vertically, and the bed of powder is positioned within the (previously determined) uniform temperature region of the furnace. Under a flow of air of 100±10 sccm, the furnace temperature is ramped from ambient to 275° C. at 10° C./min, and is held at that temperature for eight hours. The gas is switched to nitrogen (same flow rate), and the furnace temperature is ramped to 615° C. at 2° C./min. The temperature is held at 615° C. for two hours, then the furnace is allowed to cool to ambient temperature while under nitrogen flow. This yields 11.2 g of a black powder.

Example 2

The procedure of Example 1 is repeated, except that 7.0 g precursor are used, and after holding for eight hours in air at 275° C. and switching to nitrogen, the temperature is held an additional two hours at 275° C. before ramping to 615° C. This yields 6.4 g of a black solid.

Example 3

The procedure of Example 2 is repeated, except that the hold time under nitrogen at 275° C. is eight hours. This yields 6.45 g of a black solid.

Example 4

The procedure of Example 1 is followed, except that 15.0 g precursor are used, and after holding for eight hours in air at 275° C. and switching to nitrogen, the furnace is allowed to cool to room temperature to yield 14.1 g of a gray-green solid. The solid (7.1 g) is charged to a tube as in the other examples, then held at ambient temperature under a flow of nitrogen of 100±10 sccm for two hours to purge oxygen. The temperature is then ramped to 275° C. at 10° C./min, then to 615° C. at 2° C./min. The temperature is held at 615° C. for two hours, then the furnace is allowed to cool to ambient temperature while under nitrogen flow. This yields 6.7 g of a black solid.

Example 5

The procedure of Example 1 is followed, except that 7.0 g precursor are used, and after holding for eight hours in air at 275° C. and switching to nitrogen, the furnace is allowed to cool to room temperature. After reaching room temperature, the furnace is held for two hours before ramping to 275° C. at 10° C./min, then to 615° C. at 2° C./min. The temperature is held at 615° C. for two hours, then the furnace is allowed to cool to ambient temperature while under nitrogen flow. This yields 6.4 g of a black solid.

Comparative Experiment A (Not an Embodiment of the Invention)

Precursor (12.0 g) is charged as in the other examples, then held at ambient temperature under a flow of nitrogen of 100±10 sccm for two hours to purge oxygen. The temperature is then ramped to 275° C. at 10° C./min, then to 615° C. at 2° C./min. The temperature is held at 615° C. for two hours, then the furnace is allowed to cool to ambient temperature while under nitrogen flow. This yields 10.7 g of a black solid. Tellurium metal is observed on the wall of the tube downstream of the catalyst.

Comparative Experiment B (Not an Embodiment of the Invention)

The procedure of Comparative Experiment A is followed, except that 7.0 g precursor are used, and after ramping to 275° C. the temperature is held for eight hours before ramping to 615° C. This yields 6.2 g of a black solid. Tellurium metal is observed on the wall of the tube downstream of the catalyst.

Comparative Experiment C (Not an Embodiment of the Invention)

Precursor (15.0 g) is charged as in the other examples, then held at ambient temperature under a flow of nitrogen of 100±10 sccm for two hours to purge oxygen. The temperature is then ramped to 275° C. at 10° C./min, and held at that temperature for eight hours. The furnace is allowed to cool to room temperature to yield 14.4 g of a gray-green solid. The solid (7.0 g) is charged to a tube as in the other examples, then held at ambient temperature under a flow of nitrogen of 100±10 sccm for two hours to purge oxygen. The temperature is then ramped to 275° C. at 10° C./min, then to 615° C. at 2° C./min. The temperature is held at 615° C. for two hours, then the furnace is allowed to cool to ambient temperature while under nitrogen flow. This yields 6.4 g of a black solid. Tellurium metal is observed on the wall of the tube downstream of the catalyst.

Comparative Experiment D (Not an Embodiment of the Invention)

The procedure of Example 1 is followed, except that 7.0 g precursor are used, and upon reaching 275° C., the atmosphere is immediately switched to nitrogen and ramping to 615° C. is initiated. Yield 6.2 g black solid. Te metal is observed on the wall of the tube downstream of the catalyst.

These examples and experiments show that the process of the invention surprisingly show that the process of the invention results in an increased amount of retained tellurium and a decreased amount of phase M2.

TABLE 1

Summary of calcination conditions and phase and elemental compositions of catalysts. Te levels are expressed as molar ratios Te/(Mo + V + Nb).

| sample | initial purge | ramp and hold atmosphere | hold time (h) | second hold atmosphere | second hold time (h) | cool-down purge | phase M2 (%) | Te level (relative) |
|---|---|---|---|---|---|---|---|---|
| Ex. 1 | — | air | 8 | — | — | — | 4 | 0.17 |
| Ex. 2 | — | air | 8 | N2 | 2 | — | 3 | 0.17 |
| Ex. 3 | — | air | 8 | N2 | 8 | — | 7 | 0.17 |
| Ex. 4 | — | air | 8 | — | — | N2 | 3 | 0.17 |
| Ex. 5 | — | air | 8 | — | — | N2 | 6 | 0.17 |
| Comp. Ex. A | N2 | N2 | 0 | — | — | — | 17 | 0.14 |
| Comp. Ex. B | N2 | N2 | 8 | — | — | — | 17 | 0.14 |
| Comp. Ex. C | N2 | N2 | 8 | — | — | N2 | 17 | 0.14 |
| Comp. Ex. D | — | air | 0 | — | — | — | 17 | 0.14 |

What is claimed is:

1. A process for preparing a propane oxidation catalyst, the process comprising: (a) preparing a catalyst precursor; (b) pre-calcining the catalyst precursor in an oxygen-containing gas at a temperature of less than 330° C. until the weight of the precursor stabilizes to obtain a pre-calcined precursor; then (c) calcining the pre-calcined precursor to obtain the catalyst, wherein step (b) is maintained for at least 5 hours, and wherein the catalyst comprises an orthorhombic phase M1 and a pseudo-hexagonal phase M2, and wherein the amount of phase M2 in the catalyst is less than 12%.

2. The process of claim 1 wherein step (b) is maintained for at least 6 hours.

3. The process of claim 1 wherein step (b) is maintained for at least 8 hours.

4. The process of claim 1, wherein the amount of phase M2 in the catalyst is less than 10%.

5. The process of claim 1, wherein the amount of phase M2 in the catalyst is less than 8%.

6. The process of claim 1, wherein the amount of phase M2 in the catalyst is less than 7%.

7. The process of claim 1, wherein the temperature of step (b) is less than 310° C.

8. The process of claim 1, wherein the catalyst is represented by the formula $A_aV_bN_cX_dZ_eO_f$ wherein A is at least one element selected from the group consisting of Mo and W, N is at least one element selected from the group consisting of Te and Sb, X is at least one element selected from the group consisting of Nb, Ta, Ti, Al, Zr, Cr, Mn, Fe, Ru, Co, Rh, Ni, Pt, Sb, Bi, B, In, As, Ge, Sn, Hf, Pb, P, Pm, Eu, Gd, Dy, Ho, Er, Tm, Yb and Lu, and Z is at least one element selected from the group consisting of Zn, Ga, Ir, Sm, Pd, Au, Ag, Cu, Sc, Y, Pr, Nd and Tb; and wherein, when a=1, b=0.01 to 1.0, c=0.01 to 1.0, d=0.01 to 1.0, e=0 to 0.1 and f is dependent on the oxidation state of the other elements.

9. The process of claim 1, wherein A=Mo, N=Te, and X=Nb.

* * * * *